United States Patent [19]

Bach et al.

[11] 4,434,148
[45] Feb. 28, 1984

[54] WORKING UP OF THE RESIDUAL GASES RESULTING FROM THE PRODUCTION OF CYANURIC CHLORIDE

[75] Inventors: Gerhard Bach, Frechen; Friedhelm Geiger, Erlensee; Werner Heimberger; Gerd Schreyer, both of Hanau; Horst Hillenbrand, Wesseling, all of Fed. Rep. of Germany

[73] Assignee: Degussa Aktiengesellschaft, Frankfurt, Fed. Rep. of Germany

[21] Appl. No.: 81,555

[22] Filed: Oct. 3, 1979

[30] Foreign Application Priority Data

Oct. 5, 1978 [DE] Fed. Rep. of Germany ....... 2843383

[51] Int. Cl.$^3$ ............................................. C01B 21/18
[52] U.S. Cl. .................................................. 423/379
[58] Field of Search ........................................ 423/379

[56] References Cited

U.S. PATENT DOCUMENTS

| 3,197,273 | 7/1965 | Trickey | 423/383 |
| 3,535,091 | 10/1970 | Trickey | 423/379 |
| 3,567,406 | 3/1971 | Evers | 423/379 |
| 3,568,408 | 3/1971 | Riethmann et al. | 55/71 |
| 3,763,157 | 10/1973 | Syrvanaravana et al. | 423/371 |
| 3,825,658 | 7/1974 | Eckert, Jr. et al. | 423/379 |

FOREIGN PATENT DOCUMENTS

| 1934856 | 7/1973 | Fed. Rep. of Germany | 423/371 |
| 2106675 | 12/1976 | Fed. Rep. of Germany | 423/371 |
| 918707 | 2/1947 | France | 423/371 |
| 1311400 | 3/1953 | France | 423/371 |
| 2310964 | 12/1976 | France | 423/371 |

*Primary Examiner*—O. R. Vertiz
*Assistant Examiner*—Wayne A. Langel
*Attorney, Agent, or Firm*—Cushman, Darby & Cushman

[57] ABSTRACT

The residual gases obtained in the production of cyanuric chloride having a pressure of 1–5 bar (absolute) preferably 1–4 bar, are worked up by leading them into the lower portion of a column, reacted in the column with at least the equivalent amount of hydrogen cyanide to form cyanogen chloride and led in countercurrent flow to the water charged to the upper portion of the column whereupon the aqueous solution of cyanogen chloride formed is withdrawn from the lower portion of the column and preferably is returned into the production portion of the plant for recovery of the cyanogen chloride while the purified waste gas of the column leaves in the upper portion of the column.

8 Claims, 1 Drawing Figure

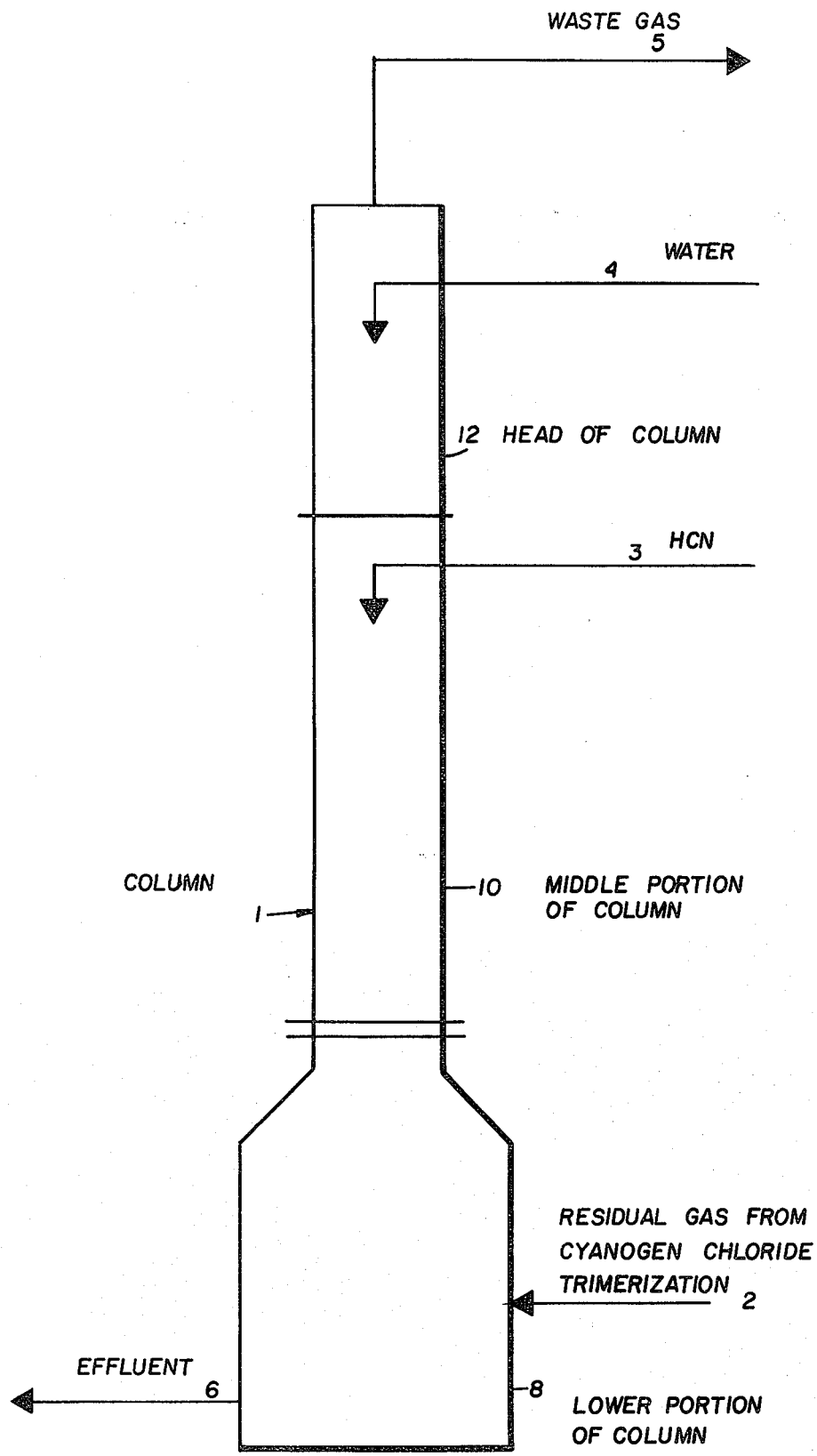

WORKING UP OF THE RESIDUAL GASES RESULTING FROM THE PRODUCTION OF CYANURIC CHLORIDE

BACKGROUND OF THE INVENTION

It is known to produce cyanogen chloride (see Huemer German Pat. No. 827,358, Huemer German Pat. No. 842,067 and Ullmann's Encyclopädie der technischen Chemie, 3rd edition, Vol. 5 (1954) page 624) by reacting hydrogen cyanide and chlorine in the presence of water to form cyanogen chloride and hydrochloric acid to drive off the cyanogen chloride from the aqueous solution by heating, to dry over calcium chloride and to trimerize to cyanuric chloride in a subsequent reactor at 200°–500° C. in the presence of activated carbon. The entire disclosure of the two German patents and the page from Ullmann are hereby incorporated by reference and relied upon.

The cyanuric chloride vapors leaving the trimerization reactor go to a cooled separator from which the cyanuric chloride is discharged in crystalline form. The waste gases, which chiefly consist of unreacted cyanogen chloride, as well as chlorine, hydrogen chloride and inert gases such as phosgene or carbon tetrachloride, are washed with water in countercurrent flow in one or more columns and then pass into the open air, while the cyanogen chloride and chlorine containing aqueous solution is led back into the chlorination portion.

The hydrogen chloride formed as byproduct in the chlorination of hydrogen cyanide is withdrawn from the plant in the form of a dilute aqueous hydrochloric acid, while the water withdrawn in the form of hydrochloric acid is replaced again by the addition of fresh water. The supply of fresh water is so regulated that there always can be recovered an about 12 weight % solution of aqueous hydrochloric acid. Hydrochloric acid concentrations above 12 weight % to be sure can be obtained, however, simultaneously there would be greatly increased the saponification of the first dissolved cyanogen chloride with formation of ammonium chloride which remains in the hydrochloric acid, and carbon dioxide which passes with the cyanogen chloride into the trimerization reactor. It has likewise been shown that even at a hydrocloride acid concentration of 13 weight % there already is a trifling saponification of the cyanogen chloride to the degree of about 2%.

The trimerization of the dried cyanogen chloride is especially advantageously carried out in the presence of about 0.5–3 weight % of chlorine. However, since the trimerization of the cynanogen chloride only progresses to an extent of about 98–99% there is obtained a residual gas after the cooled separatory chamber, which according to the reaction conditions contains about 20–50 weight % cyanogen chloride, 30–70 weight % chlorine and 10–30 weight % carbon dioxide.

Because of the good solubility of cyanogen chloride in water it is readily possible to wash out the cyanogen chloride from the residual gas by a corresponding countercurrent absorption with water, whereby the aqueous solution formed which contains chlorine and cyanogen chloride, again can be recycled into the chlorination portion.

However, on account of the low solubility of chlorine in water and on account of the proportionally high content of carbon dioxide which appears as carrier gas in the absorption in water and thus opposes a complete absorption of cyanogen chloride and chlorine, the absorption of chlorine in water in insufficient. Therefore residual gas leaving the absorption column still contains 15–70 weight % of chlorine, besides 30–85 weight % of carbon dioxide and nitrogen.

If it is desired to wash out the chlorine by water, then such a large amount of water is needed that in a recycling into the chlorination portion there would occur necessarily a diluted hydrochloric acid of a type, which would be uneconomical and must be destroyed by neutralization. However, this leads to an unpermittedly high salt fraction in the waste water.

However, for environmentally protective reasons the untreated residual gas cannot be given off directly to the atmosphere. Therefore a known method treats the residual gas with aqueous alkalis, as e.g. soda lye. However thereby there is formed an aqueous solution which contains besides hypochlorite also alkali chloride and carbonate and only after reduction of the hypochlorite and neutralization can be delivered to the waste water.

To be sure the mentioned methods permit the production of a pure outgoing air; however, it is uneconomical to a high degree and loads the waste water with high amounts of salts, i.e. it converts the outgoing air problem to a waste water problem.

SUMMARY OF THE INVENTION

It has now been found that the residual gas containing chlorine and cyanogen chloride obtained in the trimerization of cyanogen chloride can be easily removed is this residual gas having a pressure of 1–5 bar (absolute), preferably having a pressure of 1–4 bar (absolute) is led into the lower portion of a column, reacting in the column, with at least the equivalent amount of hydrogen cyanide to form cyanogen chloride and led in countercurrent flow to the water, delivered to the upper portion of the column whereupon the aqueous solution of cyanogen chloride formed is withdrawn from the lower portion of the column and preferably is returned into the production of the plant for the recovery of the cyanogen chloride, while the purified waste gas leaves the column in the upper portion thereof.

As absorption columns there can be used above all those which contain installations such as trays or packings.

The supplying of the residual gases and hydrogen cyanide can take place in any desired manner; thus it is possible to lead both gaseous components through a common or separated line into the lower portion of the absorption column.

However, it is also possible to use a larger than equivalent amount of hydrogen cyanide, and in fact this is preferred. The excess is not critical and depends only on the dimension of the column.

Besides the hydrogen cyanide can be added in aqueous solution. This aqueous hydrogen cyanide solution is preferably a portion of the circulating solution in the portion of the apparatus for the production of cyanogen chloride and generally contains besides 0.9 to 2.5 weight % hydrogen cyanide 3 to 6 weight % cyanogen chloride.

The amount of fresh water added to the top of the column is so measured that the column effluent can be recycled into the portion for the production of cyanogen chloride and hydrochloric acid is formed there with a concentration of about 3–15 weight %, preferably 10–13 weight %.

The reaction of the residual gas with hydrogen cyanide takes place at a temperature of 0°–100° C., preferably at 10°–60° C. Higher pressures than 5 bar (absolute) are possible, but industrially are not very significant.

A cooling of the absorption column to lead off the heat of reaction generally is necessary only in the lower range of the above mentioned temperatures, i.e. below 10° C.

The advance in the art of the process of the invention is first in the possibility that the chlorine contained in the residual gas can be removed and that also the cyanogen chloride still present together with the chlorine can be recovered in a single step and can be supplied for further use. The carrying out of the process is very simple and the resulting purified waste gas is completely free from injurious materials.

BRIEF DESCRIPTION OF THE DRAWING

The single FIGURE of the drawings shows in schematic fashion an apparatus for carrying out the process of the invention.

Referring more specifically to the drawings the residual gas from the trimerization of cyanogen chloride is led via line 2 into the lower portion 8 of column 1. In the middle portion 10 there is led in via line 3 hydrocyanic acid containing water or a portion of the circulating solution formed in the part of the apparatus used for the production of cyanogen chloride, i.e., the upper portion of the column 1 is operated as a washer, the lower portion as a reactor.

The amount of this hydrocyanic acid containing solution depends first on the reactable chlorine content of the residual gas and secondly on the concentration of the hydrocyanic acid present in the aqueous solution. The higher the chlorine content is the more hydrogen cyanide is needed for quantitative reaction. This amount can either be supplied by a smaller amount of solution which is concentrated in hydrocyanic acid or by a correspondingly greater amount of weaker solution of hydrocyanic acid.

Water is supplied to the head or top 12 of the column 1 via line 4.

The purified waste gas leaves the column via line 5.

The effluent from column 1 is withdrawn via line 6 and preferable supplied to the portion of the apparatus for the production of cyanogen chloride (not shown).

Since the hydrogen cyanide containing aqueous solution is returned to the part of the apparatus for the production of cyanogen chloride, there does not occur an environmental problem through the use of an excess of hydrogen cyanide.

The advance in the art of the process of the invention is directly in the fact that not only is there formed a completely chlorine free waste gas which can be discharged into the atmosphere but simultaneously the chlorine in the waste gas can be converted into cyanogen chlorine and therewith not lost for the production of cyanogen chloride.

Besides hereby there is also solved the problem of the formation of dilute, aqueous, useless hydrochloric acid.

The process can comprise, consist essentially of or consists of the steps set forth with the stated materials.

Unless otherwise indicated all parts and percentages are by weight.

Unless otherwise indicated the temperature is room temperature.

The invention will be further explained on the basis of the following examples:

DESCRIPTION OF THE PREFERRED EMBODIMENTS

EXAMPLE 1

There were admitted into column 1 of the drawing 12.7 m$^3$/h of residual gas at 1.1 bar (absolute). The chlorine portion was 9.3 kg/h and the cyanogen chloride content 3.8 kg/h. For reaction of the chlorine there was added into the middle of column 1 hourly 500 liters of a circulating solution formed in the part of the apparatus for the production of cyanogen chloride. This aqueous solution contained 2.25%Δ11.3 kg of HCN and 5%Δ25 kg of cyanogen chloride. The head of the column was supplied with 10 m$^3$/h of cold water.

The waste gas (8.4 m$^3$/h) leaving the head of the column was free from chlorine, cyanogen chloride and hydrogen cyanide.

The effluent from column 1 was again lead to the part of the apparatus for the production of the cyanogen chloride.

EXAMPLE 2

There were admitted into column 1 of the drawing 58 m$^3$/h of residual gas at 1.1 bar (absolute). The chlorine portion was 15.2 kg/h and the cyanogen chloride content 24.0 kg/h. For reaction of the chlorine there was added into the middle of column 1 hourly a solution of 16.7 kg of hydrogen cyanide in 600 liters of water. The head of the column was supplied with 9.7 m$^3$/h of water. The waste gas (44.4 m$^3$/h) leaving the head of column 1 was free from chlorine, cyanogen chloride and hydrogen cyanide.

The effluent from column 1 which was led to the part of the apparatus for the pruduction of cyanogen chloride contained 10.91 kg/h of HCN and 37.2 kg/h of cyanogen chloride.

EXAMPLE 3

There were led into the lower portion of a pressure column 1 filled with Raschig rings both 62 m$^3$/h of residual gas having a Cl$_2$ content of 15.1 kg/h and also 520 kg/h of a HCN containing solution having an HCN content of 20 kg/h. The head of the column 1 was supplied with 10 m$^3$/h of water.

At the head of the column, which was operated at 45° C. there was located an automatic pressure-retaining valve which was adjusted to 3.5 bar (absolute). To the rear of this valve the waste gas was released to atmospheric pressure.

The waste gas leaving column 1 was free from chlorine, cyanogen chloride and hydrogen cyanide.

The effluent of column 1 which was supplied to the part of the plant for the production of cyanogen chloride contained 14.26 kg/h of HCN and 13.1 kg/h of HCN.

There is incorporated by reference the entire disclosure of German priority application No. P 28 43 383.2-44.

What is claimed is:

1. A process for working up the chlorine containing residual gases obtained in the production of cyanuric chloride by the trimerization of cyanogen chloride and consisting chiefly of unreacted cyanogen chloride, as well as chlorine, hydrogen chloride and inert gases comprising leading them into the lower portion of a column at 1–5 bar (absolute), reacting the gases in the column with at least the equivalent amount of hydrogen cyanide to form cyanogen chloride, charging water into the upper portion of the column, leading the cyanogen chloride formed in countercurrent flow to said water, and withdrawing an aqueous solution of cyanogen chloride from the lower portion of the column and removing the purified waste gas from the upper portion of the column.

2. The process of claim 1 wherein the lower portion of the column is at 1-4 bar.

3. The process of claim 2 wherein the cyanogen chloride solution withdrawn from the column is returned to the production portion of a plant for recovery of the cyanogen chloride.

4. The process of claim 2 wherein the temperature is 10°-60° C.

5. The process of claim 2 wherein the hydrogen cyanide added is part of a solution circulating in the portion of a plant producing cyanogen chloride.

6. The process of claim 1 wherein the hydrogen cyanide added is part of a solution circulating in the portion of a plant producing cyanogen chloride.

7. The process of claim 1 wherein the temperature is 0°-100° C.

8. The process of claim 7 wherein the temperature is 10°-60° C.

* * * * *